United States Patent [19]
Santillo, Jr.

[11] Patent Number: 6,117,461
[45] Date of Patent: *Sep. 12, 2000

[54] POWDERED FOOD COMPOSITION

[76] Inventor: Humbart D. Santillo, Jr., 5010 Glenwood Dr., Williamsville, N.Y. 14221

[ * ] Notice: This patent issued on a continued prosecution application filed under 37 CFR 1.53(d), and is subject to the twenty year patent term provisions of 35 U.S.C. 154(a)(2).

[21] Appl. No.: 08/846,557

[22] Filed: Apr. 30, 1997

Related U.S. Application Data

[62] Division of application No. 07/955,919, Oct. 2, 1992, Pat. No. 5,656,310.
[51] Int. Cl.[7] .................................................. A23L 1/28
[52] U.S. Cl. ........................... 426/61; 426/63; 426/599; 426/640; 426/800; 426/801
[58] Field of Search ................... 426/61, 63, 590, 426/595, 599, 615, 640, 800, 801

[56] References Cited

U.S. PATENT DOCUMENTS

| | | | |
|---|---|---|---|
| 1,204,880 | 11/1916 | Kern | 426/590 |
| 1,204,881 | 11/1916 | Kern | 426/590 |
| 3,433,644 | 3/1969 | Ganske et al. | 426/590 |
| 3,615,674 | 10/1971 | Johnston | 426/590 |
| 3,615,721 | 10/1971 | Silberman | 426/52 |
| 4,233,334 | 11/1980 | Owades | 426/590 |
| 4,544,558 | 10/1985 | Pellegrini | 426/52 |
| 4,716,044 | 12/1987 | Thomas et al. | 426/51 |
| 5,096,719 | 3/1992 | Gresch | 426/51 |

*Primary Examiner*—Leslie Wong
*Attorney, Agent, or Firm*—Harris Beach Wilcox LLP

[57] ABSTRACT

A food composition containing from about 80 to about 98 parts by weight of a first plant material derived from fruit and/or vegetable juices, from about 1 to about 10 parts by weight of a second plant material derived from fruit and/or vegetable fiber, and from about 1 to about 10 parts by weight of enzyme material selected from the group consisting of amylase, protease, lipase, cellulase, and mixtures thereof. Preferably, the first and second materials are each dried before being combined, and the enzyme material is derived from at least one species of Aspergillus mold.

12 Claims, 1 Drawing Sheet

POWDERED FOOD COMPOSITION

This application is a division of application Ser. No. 07/955,919 filed Oct. 2, 1992 which application is now U.S. Pat. No. 5,656,310.

FIELD OF THE INVENTION

A stable, concentrated, powdered food composition which is relatively easy to digest is disclosed.

BACKGROUND OF THE INVENTION

Powdered food compositions are well known to those skilled in the art. Thus, for example, "Tang" is a commercially available powdered, synthetic organic drink.

Digestion is the chemical process by which nutrient molecules are converted within a body to forms usable by the cells. The chemical reactions occurring during digestion are facilitated by enzymes, which are catalysts, usually formed of protein, which have specific actions and optimum activities at a definite pH value.

Enzymes are produced by the D.N.A. replication process in living beings. There is a substantial amount of evidence indicating that the aging process, in part, results from a reduction in the amount of enzyme produced by a living body. Thus, as is disclosed at page 14 of Humbart Santillo's "Food Enyzmes" (Hohm Press, Prescott, Arizona, 1991), "A further experiment in relation to saliva and its amylase content was performed . . . . Used in this experiment were young adults from the ages of 21 to 31 and another group ranging from age 69 to 100. It was shown that the younger group had 30 times more amylase in their saliva than the elderly group."

There thus is a need for nutritional supplements which, in addition to nutrients, contain enzymes which will facilitate the digestion of the nutrients. It would be especially desirable if such food supplements would contain enzymes which could function in the stomach and/or the intestines of a user and which would not be destroyed in the process of digestion.

Most enzymes have an optimum pH value at which they function, and for most enzymes this pH value is in the range of from about 4.5 to about 8.0; see, e.g., page 354 of John M. DeMan's "Principles of Food Chemistry" (Van Nostrand Reinhold Company, New York, New York, 1980). It has been said that ". . . the presence of too many hydrogen or hydroxy ions interferes with the conforming shape of the enzymes;" see, e.g., page 44 of Gabrille I. Edwards' "Biology the Easy Way" (Barrons Educational Series, Inc., New York, New York, 1990). The stomach of human beings contains gastric juice, which has a pH of about 1.0. Most enzymes are inactivated in the presence of such an acidic environment; thus, food supplements contains such enzymes will not necessarily be readily digested within the stomach.

Proteases are enzymes that split proteins into proteoses and peptones. Many enzymes, which are immune to attack by proteases in one environment, are susceptible to such attack in another environment; and thus many enzymes are destroyed when introduced into a human body.

It is an object of this invention to provide a food supplement which can be stored indefinitely at room temperature while retaining its potency.

It is another object of this invention to provide a food supplement which has substantially greater nutritive value than many of the raw foods from which it is derived.

It is yet another object of this invention to provide a food supplement which can readily be digested at least in part in the stomach of its user.

It is yet another object of this invention to provide a food supplement which furnishes one or more enzymes to the body of its user which are not destroyed during digestion.

SUMMARY OF THIS INVENTION

In accordance with this invention, there is provided a food supplement which contains a mixture of a first plant powder, a second plant powder, fiber, and at least one enzyme derived from the mold genus Aspergillus.

BRIEF DESCRIPTION OF THE DRAWING

The invention will be described by reference to the following FIGURE, in which like numerals refer to like elements, and in which.

DESCRIPTION OF THE PREFERRED EMBODIMENT

Figure 1:
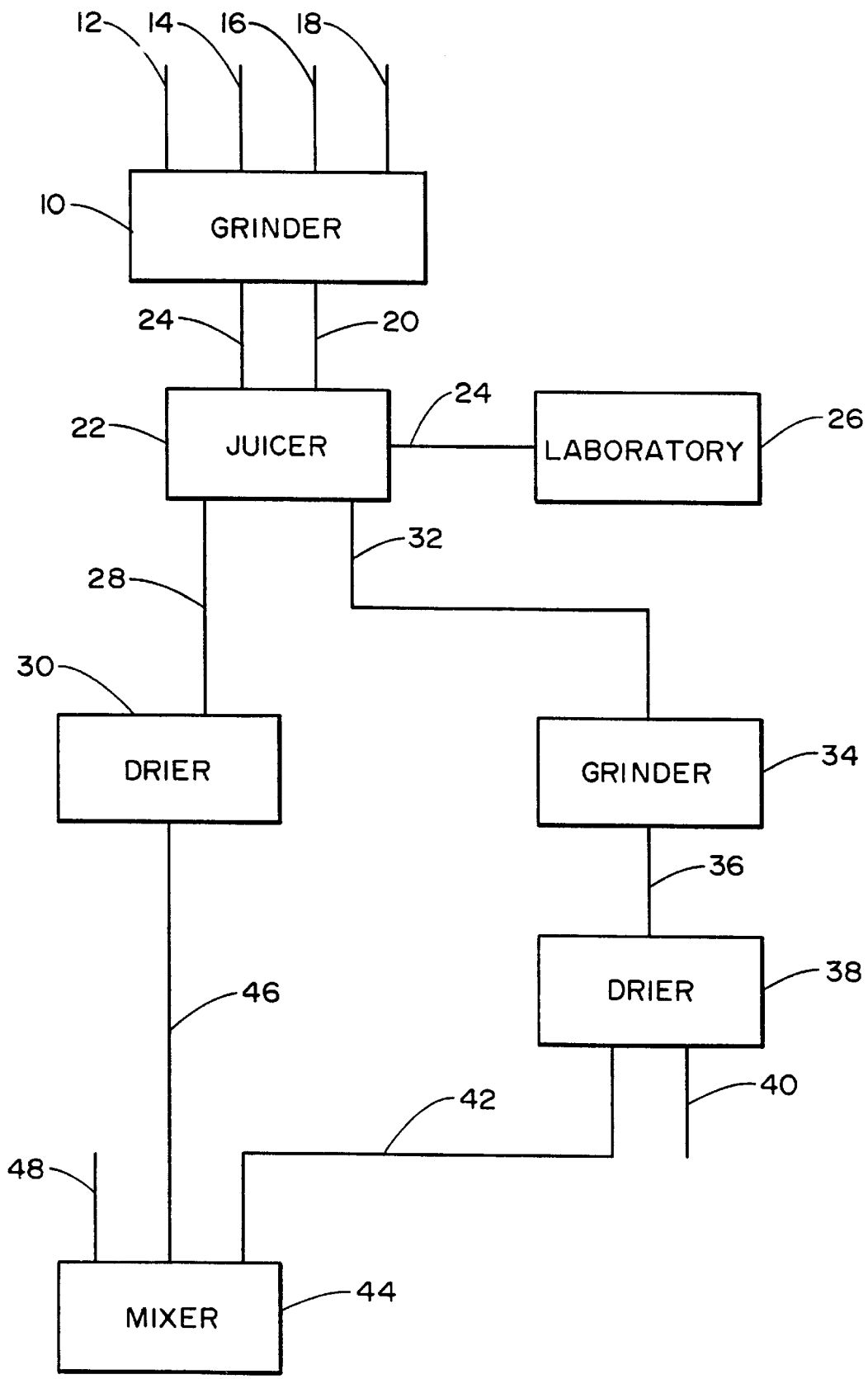
FIG. 1 is a flow diagram of a preferred process for making the composition of this invention.

FIG. 1 is a flow diagram of one preferred embodiment of the process of applicant's invention. Referring to FIG. 1, it will be seen that, to grinder 10 is charged at least two different vegetable and/or fruit materials.

Different combinations of vegetable materials, and/or fruit materials, may be charged to mixer 10 via lines 12 and/or 14 and/or 16 and/or 18. It is preferred that at least two different such materials be charged. It is more preferred that at least three different such materials be charged. In one embodiment, at least four such different materials are charged.

In one embodiment suitable for administration to children, pineapples, apples, strawberries, and oranges are charged to the grinder 10. In one aspect of this embodiment, four parts of pineapple, three parts of apples, one part of oranges, and one part of strawberries are charged to the mixer.

In another embodiment which is suitable for administration to athletes, carrots, apples, kale, watercress, beets, beet tops, and alfalfa are charged to mixer 10.

In yet another embodiment which is suitable for weight loss diets, cucumbers, lettuce, apples, carrots, and dandelions are charged to mixer 10.

In yet another embodiment, parsley, kale, spinach, chard, apples, carrots, and beet tops are charged to mixer 10.

In yet another embodiment, algae, parsley, carrots, apples, kale, and alfalfa are charged to mixer 10.

In yet another embodiment, kale, watercress, celery, carrots, and apples are charged to mixer 10.

In yet another embodiment, cabbage, broccoli, carrots, ginseng, yucca, barley, alfalfa, and carrots are charged to mixer 10.

It is preferred, when a vegetable or fruit is being charged to the mixer 10, to charge the whole vegetable or fruit. In one aspect of this embodiment, not shown, the vegetable(s) and/or fruit(s) is first cleaned prior to being charged to mixer 10.

Any conventional cleaning means may be used to clean the fruits and/or vegetables. Thus, e.g., the fruits and/or vegetables may be cleaned with water. Thus, e.g., the fruits and/or vegetables may be cleaned with solution of hydrogen peroxide.

When apple is one of the components charged to mixer 10, it is preferred that at least about 30 weight percent of the material charged to mixer 10 be made up of said apples.

When both apples and carrots are charged to mixer 10, it is preferred that they comprise at least about 70 weight percent of the total fruit and vegetable material charged to said mixer.

When a green vegetable material (such as parley, and/or kale and/or spinach and/or endive and/or dandelion) is charged to mixer 10, it is preferred that the total amount of green vegetable material so charged be less than about 15 weight percent of the total amount of vegetable and/or fruit material charged to the mixer 10.

In one embodiment, where the materials charged to mixer 10 are all fruits, dextran is also charged to the mixer. As is known to those skilled in the art, dextran is a gummy, fermentable carbohydrate from growths of *Leucoonstoc mesenteroides* on sucrose. In this embodiment, it is preferred to use at least 50 weight percent of rice dextran, by weight of the total mixture charged to mixer 10.

In one embodiment, it is preferred to grind the vegetable and/or fruit material in grinder 10 so that substantially all of the particles so produced are smaller than about 0.5 inches and, more preferably, than about 0.25 inches. Thereafter, in this embodiment, the material so ground may be passed via line 20 to juicer 22.

In another embodiment, the vegetable and/or fruit material(s) are charged directly to juicer 22 via line 24 without being subjected to a preliminary grinding step. In either event, the vegetable and/or fruit material in juicer 22 is then juiced.

Any juicer suitable for producing both juice and fibrous material from a vegetable and/or fruit material may be used as juicer 22.

The vegetable and/or fruit material charged to grinder 10 is juiced by conventional means. Thus, by way of illustration and not limitation, one may juice said materials by means of the extractor 2 and/or the screw press which are disclosed in U.S. Pat. No. 3,975,546 of Stahmann, the disclosure of which is hereby incorporated by reference into this specification.

Thus, by way of further illustration, one may juice the vegetable and/or fruit material by means of the diffuser or extractor 1 disclosed in U.S. Pat. No. 4,544,558 of Pellegrini, the disclosure of which is also incorporated by reference into this specification.

By way of yet further illustration, U.S. Pat. No. 4,716,044 of Thomas et al. discloses a process for obtaining juice from fruit in which a pumpable fluid puree of fruit and juice is first provided. The disclosure of this patent also is incorporated by reference into the specification.

In another embodiment, the juicing is conducted by means of centrifugation. In yet another embodiment, the juicing is conducted by means of augurs. In yet another embodiment, one may use commercially available juicers.

Thus, by way of further illustration, one may use the juicer sold by Trillium, Inc. of Seattle, Wash. as "The Juiceman Juicer."

The vegetable and/or fruit material in juicer is juiced until at least about 65 weight percent of the juice present in the vegetable and/or fruit material has been extracted. It is preferred to juice such material until at least about 70 weight percent of the juice has been extracted. It is even more preferred to juice said material until at least about 75 weight percent of the juice has been extracted.

One may readily determine the extent of the juicing process by taking a sample of the vegetable and/or fruit material charged to juicer 22, weighing it prior to drying, and drying it so that it contains less than about 0.1 weight percent of moisture. The difference in weight between the undried and the dried sample will be substantially equal to the amount of juice in the vegetable and/or fruit material. Thereafter, during the juicing process, one may periodically withdraw samples of the material being juiced from juicer 22 via line 24 and, in laboratory 26, thereafter determine the amount of juice in the withdrawn samples. When the amount of juice in the withdrawn sample is less than about 25 percent of the total amount of juice originally in the sample, the juicing operation may be stopped.

In general, at least about fifty weight percent of the vegetable and/or fruit material in juicer 22 is juice, and often at least about 75 weight percent of such material is comprised of juice.

Two different fractions are removed from juicer 22. A juice fraction is passed via line 28 to drier 30. A fiber fraction is passed via line 32 to grinder 34.

The juice fraction generally contains less than about 1.0 weight percent of cellulose. As is known to those skilled in the art, cellulose is a carbohydrate polymer of beta-glucose residue units with beta-1/4 linkages between glucose units; see, e.g., pages 159–162 of said "Principles of Food Chemistry" (by John DeMan). The juice fraction typically contains vitamins, minerals, trace minerals, and enzymes.

The fiber fraction, by comparison, generally contains at least about 70 weight percent of cellulose and, generally, at least about 80 weight percent of cellulose. It also often contains pectin, gums, lignins, and the like.

In drier 30, the juice fraction is dried until it contains less than about 5.0 weight percent of liquid. It is preferred to dry said juice fraction so that it contains less than about 1.0 weight percent of such liquid.

Any conventional means of drying the juice fraction may be used. Thus, for example, one may use the drying means disclosed on pages 711–759 of J. M. Coulson et al.'s "Chemical Engineering," Volume 2, Third Edition (Pergamon Press, Oxford, England, 1978).

In one preferred embodiment, the liquid fraction is subjected to spray drying in drier 30 to simultaneously dry it and form dried particles with a particle size distribution such that substantially all of the dried particles are smaller than about 420 microns. In this embodiment, one may use any of the conventional spray drying techniques known to those skilled in the art. Thus, by way of illustration, one may use one or more of the spray driers disclosed on pages 735–750 of said "Chemical Engineering, . . . ." text by Coulson et al.

Referring again to FIG. 1, the fibrous fraction is preferably passed via line 32 to grinder 34, where it preferably is comminuted until substantially all of its particles are smaller than about 420 microns. Thereafter, the powder so comminuted may be passed via line 36 to drier 38 in which the powder is preferably dried until it has a moisture content of less than about 5.0 weight percent. It is preferred to dry the powder so that it has a moisture content of less than about 1.0 weight percent.

A portion of the dried powder from drier 38 may be discarded via line 40. Another portion of such dried powder is passed via line 42 to mixer 44.

To mixer 44 is charged the dried juice extract powder via line 46, the dried fiber extract powder via line 42, and dried enzyme powder via line 48.

It is preferred to charge from about 80 to about 98 weight percent (by total weight of material in mixer 44) of the dried juice extract powder to mixer 44 via line 46. In one embodiment, at least about 90 weight percent of said dried juice extract powder is charged via line 46.

It is preferred to charge from about 1 to about 10 weight percent of the dried fiber extract powder to mixer 44 via line 42. In one embodiment, from about 2 to about 6 weight percent of such dried fiber extract powder is charged. In another embodiment, from about 3 to about 5 weight percent of said dried fiber extract powder is charged.

It is preferred to charge from about 1 to about 10 weight percent of one or more of the enzymes described below to mixer 44 via line 48. In one embodiment, from about 1 to about 5 weight percent of such enzyme(s) is charged to mixer 44.

The enzymes used in applicant's process preferably are produced by a species of Aspergillus. As is known to those skilled in the art, Aspergillus is a genus of molds, many of which are parasitic.

In one preferred embodiment, the enzyme(s) used is selected from the group consisting of: (1) alpha-amylase, which is classified as a carbohydrase, which is obtained from *Aspergillus oryzae,* and which has I.U.B. (International Union of Biochemists) number 3.2.1.1., (2) protease, which is obtained from *Aspergillus oryzae,* and which has I.U.B. number 3.4.21.14, (3) lipase, which is obtained from *Aspergillus niger,* and which has I.U.B. number 3.1.1.3, (4) cellulase, which is classified as a carbohydrase, which is obtained from *Aspergillus niger,* and which has I.U.B. number 3.2.1.4, and (5) mixtures thereof. As is known to those skilled in the art, these enzymes, and their associated I.U.B. numbers, are described in the "Food Chemicals Codex," 3rd edition (National Academy Press, Washington, D.C., 1981).

These enzymes are commercially available and may be purchased, either singly or in combination, from the National Enzyme Company, Inc., Post Office Box 128, Forsyth, Mo. 65653. Thus, by way of illustration one may purchase "Formula 1" (which contains protease, amylase, lipase, and cellulase enzymes), "Formula 2" (which contains the amylase, protease, lipase, and cellulase enzymes and, in addition, 200 million viable *Lactobacillus acidophilus* organisms per 220 milligrams of composition), "Formula 6" (which contains the amylase, protease, lipase, and cellulase enzymes and, additionally, marshmallow root and rose hips), "Formula 7" (which contains the amylase, lipase, and protease enzymes plus, in addition, safflower petals), "Formula 9" (which contains the protease, amylase, and lipase enzymes and, additionally, alfalfa juice concentrate, parsley leaf, horsetail rush, and rose hips), "Formula 10" (which contains invertase, amylase, protease, lipase, and cellulase enzymes and, additionally, brewers yeast, gotu kola, rose hips, and urea), "Formula 12" (which contains the cellulase, amylase, protease, and lipase enzymes and, additionally, citrus bioflavonoids, burdock root, and organic germanium), "Formula 13" (which contains lipase, amylase, protease, and cellulase enzymes and, in addition, wheat germ, lecithin, and kelp, "Formula 14" (which contains the protease, amylase, lipase, and cellulase enzymes and, in addition, marine organic minerals (kelp), and irish moss, "Formula 15" (which contains protease, amylase, lipase, and cellulase enzymes and, in addition, spirulina plankton, alfalfa juice concentrate, and parsley leaf), "Formula 16" (which contains protease, amylase, and lipase enzymes and, in addition, calcium lactate), "Formula 17" (which contains protease, amylase, and lipase enzymes and, in addition Pau D'Arco, Yellow Dock, Echinacea, Mullein, and Organic Germanium), "Formula 19" (which contains the protease, amylase, and lipase enzymes and, in addition, calcium gluconate and magnesium gluconate), and the like.

In one embodiment, it is preferred to add each of the aforementioned enzymes to mixer 44. It will be understood that, when said enzymes are added and, additionally, other material(s) are also added (such as, e.g., calcium gluconate), only the amount of enzyme(s) added is to be used in calculating the concentration of the enzyme(s).

The enzyme(s) to be added are preferably in dry, powder form and, thus, contain less than about 5.0 weight percent of moisture and, also, have a particle size such that substantially all of their particles are smaller than about 420 microns.

The materials in mixer 44 are preferably dry mixed until a substantially homogeneous mixture is produced. Then it may be used as a whole food nutritional supplement. This supplement has a very long shelf life, retains most aromas of the materials from which it was made, is easily digestible, and provides an additional source of enzymes to a user which remain in his system after the food material(s) has been digested.

It is to be understood that the aforementioned description is illustrative only and that changes can be made in the ingredients and their proportions, and in the sequence of combinations and process steps, as well as in other aspects of the invention discussed herein, without departing from the spirit and scope of the invention as defined in the following claims.

Thus, for example, in one embodiment, instead of grinding and/or juicing and/or drying all of the vegetable and/or fruit material together, some or all of these steps may be conducted in separate operations, and the products from one or more of such steps may thereafter be combined.

What is claimed is:

1. A dried food composition, comprising:
   a) a dried plant portion derived from plant starting materials selected from the group consisting of vegetables, fruits, tubers, grains, and combinations thereof, said plant starting materials containing plant juice solids and plant fiber solids in a first ratio of said juice solids to said fiber solids; and
   b) a dried enzyme portion including enzymes suitable for digestion of at least some of said plant portion after ingestion of said composition by a consumer;
   wherein a second ratio of juice solids to fiber solids in said dried supplement is greater than said first ratio in said plant starting materials.

2. A food composition in accordance with claim 1 wherein said plant starting materials comprise at least two different plant materials.

3. A food composition in accordance with claim 1 wherein said second ratio is between about 4:1 and about 50:1.

4. A food composition in accordance with claim 1 wherein said enzyme portion is between about 1 and about 10 percent by weight of said composition.

5. A food composition in accordance with claim 1 wherein said enzyme portion includes enzymes selected from the group consisting of amylases, proteases, lipases, cellulases, and combinations thereof.

6. A food composition in accordance with claim 1 wherein at least a portion of said enzyme portion is derived from Aspergillus.

7. A food composition in accordance with claim 1 wherein said enzyme portion contains plant materials distinct from said plant starting materials from which said dried juice and fiber amounts have been derived.

8. A food composition in accordance with claim 1 further comprising an amount of *Lactobacillus acidophilus*.

9. A food composition in accordance with claim 1 further comprising an amount of calcium gluconate.

10. A food composition in accordance with claim 1 wherein said composition contains less than about 5 percent water by weight.

11. A food composition in accordance with claim 1 wherein said composition is in the form of a powder.

12. A food composition in accordance with claim 1 wherein said plant starting materials are selected from the group of plant parts consisting of fruits, seeds, roots, tubers, leaves, stems, stalks, flowers, and combinations thereof.

* * * * *